US008062898B2

(12) United States Patent
Pauli et al.

(10) Patent No.: US 8,062,898 B2
(45) Date of Patent: Nov. 22, 2011

(54) SELECTION AND RATIONAL DEVELOPMENT OF SOLVENT SYSTEMS IN COUNTER-CURRENT CHROMATOGRAPH

(75) Inventors: Guido F. Pauli, Chicago, IL (US); John Brent Friesen, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 861 days.

(21) Appl. No.: 11/876,545

(22) Filed: Oct. 22, 2007

(65) Prior Publication Data

US 2008/0127720 A1    Jun. 5, 2008

Related U.S. Application Data

(60) Provisional application No. 60/853,079, filed on Oct. 20, 2006.

(51) Int. Cl.
*G01N 30/00* (2006.01)
(52) U.S. Cl. .................................................. 436/161
(58) Field of Classification Search ................... 436/161
See application file for complete search history.

(56) References Cited

U.S. PATENT DOCUMENTS

| | | | |
|---|---|---|---|
| 4,051,025 | A | 9/1977 | Ito |
| 4,228,009 | A | 10/1980 | Ito |
| 5,217,608 | A | 6/1993 | Conway |
| 5,332,504 | A | 7/1994 | Ito et al. |
| 5,354,473 | A | 10/1994 | Ito et al. |
| 5,449,461 | A | 9/1995 | Ito |
| 5,770,083 | A | 6/1998 | Ma et al. |

(Continued)

FOREIGN PATENT DOCUMENTS

EP    0 808 455    11/1997
(Continued)

OTHER PUBLICATIONS

Lee et al., "The application of true countercurrent chromatography in the isolation of bioactive natural products", Journal of Natural Products, vol. 52, No. 4, pp. 706-710, 1989.*

(Continued)

*Primary Examiner* — Jill Warden
*Assistant Examiner* — Monique Cole
(74) *Attorney, Agent, or Firm* — Greenlee Sullivan P.C.

(57) ABSTRACT

Application of a reference mixture of natural products for systematic analysis and comparison of the properties of biphasic solvent systems in counter-current/partition chromatography. Because the reference mixture is comprised of compounds with varying polarities, functional groups, and structural features it provides a rational method for mapping the optimal resolution polarity range of a particular solvent system. The mapping of optimal resolution polarity ranges of solvent systems provided for the description of the overall optimal resolution polarity range of a solvent system family, comprised of the same solvents in different proportions. By comparing the reference mixture performance in the individual members of a solvent system family, the solvent system that best functions as the representative of, or portal to, the solvent system families is determined. Use of the reference mixture also afforded a method to compare the overall optimal resolution polarity ranges of solvent system families. Based on performance of reference mixture chromatograms, the CCC properties of solvent systems, can be compared and their CCC potential examined. The methods of the invention employing the reference mixture provides was used to identify a quaternary solvent system, hexane/t-butylmethylether/acetonitrile/water (HterAcWat), which was found to be useful for CCC of mixtures containing natural products.

18 Claims, 9 Drawing Sheets

U.S. PATENT DOCUMENTS

| | | | |
|---|---|---|---|
| 6,503,398 | B2 | 1/2003 | Ma et al. |
| 7,225,079 | B2 | 5/2007 | Gjerde et al. |
| 2003/0054567 | A1 | 3/2003 | Miyoshi et al. |
| 2008/0201085 | A1 | 8/2008 | Pauli et al. |

FOREIGN PATENT DOCUMENTS

| | | |
|---|---|---|
| WO | WO 03/087807 | 10/2003 |

OTHER PUBLICATIONS

Baderschneider et al. (2000) "Isolation and Characterization of Novel Stilbene Derivatives from Riesling Wine," *J. Agric. Food Chem.* 48:2681-2686.

Baderschneider et al. (2001) "Isolation and Characterization of Novel Benzoates, Cinnamates, Flavonoids, and Lignans from Riesling Wine and Screening for Antioxidant Activity," *J. Agric. Food Chem.* 49:2788-2798.

Berthod et al. (Jul. 2005) "Using the Liquid Nature of the Stationary Phase: The Elution-Extrusion Method," *J. Liq. Chromatogr. Relat. Technol.* 28(12-13):1851-1866.

Berthod, A. (Sep. 8, 2006) "Band Broadening Inside the Chromatographic Colum: The Interest of a Liquid Stationary Phase," *J. Chromatogr. A.* 1126(1-2):347-356.

Berthod et al. (2003) "Elution-Extrusion Countercurrent Chromatography. Use of the Liquid Nature of the Stationary Phase to Extend the Hydrophobicity Window," *Anal. Chem.* 75(21):5886-5894.

Berthod et al. (2005) "Alkane Effect in the Arizona Liquid Systems Used in Countercurrent Chromatography," *Anal. Bioanal. Chem.* 383:327-340.

Berthod et al. (Dec. 15, 2000) "Test to Evaluate Countercurrent Chromatographs: Liquid Stationary Phase Retention and Chromatographic Resolution," *J. Chromatogr. A* 902(2):323-335.

Berthod et al. (2007) "Elution-Extrusion Countercurrent Chromatography: Theory and Concepts in Metabolic Analysis," *Anal. Chem.* 79:3371-3382.

Berthod et al. (2004) "Determination of Liquid-Liquid Partition Coefficients by Separation Methods," *J. Chromatogr. A* 1037:3-14.

Berthod et al. (2000) "Countercurrent Chromatography: Fundamentally a Preparative Tool," *Adv. Chromatogr.* 40:503-538.

Cao et al. (Jun. 2003) "Separation of Dammarane-Saponins from Notoginseng, Root of *Panax notoginseng* (Burk.) F.H. Chen, by HSCCC Coupled with Evaporative Light Scattering Detector," *J. Liq. Chromatogr. Relat. Technol.* 26(9-10):1579-1591.

Cao et al. (Sep. 10, 1999) "Separation and Purification of Isoflavones from *Pueraria lobata* by High-Speed Counter-Current Chromatography," *J. Chromatogr. A* 855(2):709-713.

Chadwick et al. (2004) "Estrogens and Congeners from Spent Hops (*Humulus lupulus*)," *J. Nat. Prod.* 67(12):2024-2032.

Conway, W.D. (Jun. 2001) "An Indexing Scheme for Optimizing the Choice of Biphasic Systems for CCC 1," *J. Liq. Chromatogr. Relat. Technol.* 24(11-12):1555-1573.

Degenhardt et al. (2000) "Rapid Isolation of Malvidin 3-Glucoside from Red Wine by High Speed Countercurrent Chromatography (HSCCC)," *Vitis* 39:43-44.

Degenhardt et al. (2001) "Isolation and Purification of Isoflavones from Soy Flour by High-Speed Counter-Current Chromatography," *Eur. Food Res. Technol.* 213:277-280.

El Tayer e3t al. (1991) "Measurement of Partition-Coefficients by Various Centrifugal Partition Chromatographic Techniques—A Comparative-Evaluation," *J. Chromatogr.* 556:181-194.

Etter, L.S. (1993) "Nomenclature for Chromatography," *Pure Appl. Chem.* 65:819-872.

Foucault, L. (May 29, 1998) "Counter-Current Chromatography: Instrumentation, Solvent Selection and Some Recent Applications to Natural Product Purification," *J. Chromatogr. A* 808(1-2):3-22.

Friesen et al. (Oct. 2005) "G.U.E.S.S.—A Generally Useful Estimate of Solvent Systems for CCC," *J. Liq. Chromatogr. Relat. Technol.* 28:2777-2806.

Friesen et al. (2007) "Rational Development of Solvent System Families in Countercurrent Chromatography," *J. Chromatogr. A* 1151:51-59.

Friesen et al. (Mar. 2007) "Reciprocal Symmetry Plots as a Representation of Countercurrent Chromatograms," *Anal. Chem.* 79(6):2320-2324.

Gong et al. (Jun. 2003) "Selection of Aqueous Two-Phase Solvent Systems in CCC," *J. Liq. Chromatogr. Relat. Technol.* 26(9-10):1509-1520.

Gosse et al. (Dec. 2004) "Optimization of Active Saponin, Arganine C, for Microbicidal External Use," *J. Liq. Chromatogr. Relat. Technol.* 27(12):1947-1953.

Ito, Y. (Feb. 18, 2005) "Golden Rules and Pitfalls in Selecting Optimum Conditions for High-Speed Counter-Current Chromatography," *J. Chromatogr. A* 1065(2):145-168.

Ito et al. (1982) "High-Speed Preparative Countercurrent Chromatography with a Coil Planet Centrifuge," *J. Chromatogr.* 244:247-258.

Leo, A.J. (1987) "Some Advantages of Calculating Octanol Water Partition-Coefficients," *J. Pharm. Sci.* 76:166-168.

Li et al. (Oct. 12, 2001) "Preparative Isolation and Purification of Salidroside from the Chinese Medicinal Plant *Rhodiola sachalinensis* by High-Speed Counter-Current Chromatography," *J. Chromatogr. A* 932(1-2):91-95.

Long et al. (2006) "Development of an Efficient Method for the Preparative Isolation and Purification of Chlorophyll A from a Marine Dinoflagellate *Amphidinium carterae* by High-Speed Counter-Current Chromatography Coupled with Reversed-Phase High-Performance Liquid Chromatography," *Anal. Bioanal. Chem.* 386:2169-2174.

Lu et al. (Feb. 13, 2004) "Application of Preparative High-Speed Counter-Current Chromatography for Separation of Chlorogenic Acid from *Flos lonicerae*," *J. Chromatogr. A* 1026(1-2):185-190.

Oka et al. (1991) "Systematic Search for Suitable Two-Phase Solvent Systems for High-Speed Counter-Current Chromatography," *J. Chromatogr.* 538:99-108.

Oka et al. (Mar. 14, 2003) "Purification of Quinoline Yellow Components Using High-Speed Counter-Current Chromatography by Stepwise Increasing the Flow-Rate of the Mobile Phase," *J. Chromatogr. A* 989(2):249-255.

Pan et al. (2007) "Recent Progress in Countercurrent Chromatography," *J. Liq. Chromatogr. Relat. Technol.* 30:649-679.

Peng et al. (2006) "Efficient New Method for Extraction and Isolation of Three Flavenoids from *Patrinia villosa* Juss. By Supercritical Fluid Extraction and High-Speed Counter-Current Chromatography," *J. Chromatogr. A* 1102:44-50.

Peng et al. (May 13, 2005) "Preparative Separation of Isovitexin and Isoorientin from *Patrinia villosa* Juss by High-Speed Counter-Current Chromatography," *J. Chromatogr. A* 1074(1-2):111-115.

Sales et al. (2005) "Characterization of Pigments from Different High Speed Countercurrent Chromatography Wine Fractions," *J. Agr. Food Chem.* 53(11):4536-4546.

Schwarz et al. (2004) "Investigations on Anthocyanins in Wines from *Vitis vinifera* cv. Pinotage: Factors Influencing the Formation of Pinotin A and its Correlation with Wine Age," *J. Agric. Food Chem.* 52:498-504.

Shibusawa et al. (2006) "Three-Phase Solvent Systems for Comprehensive Separation of a Wide Variety of Compounds by High-Speed Counter-Current Chromatography," *J. Chromatogr. A* 1133:119-125.

Shibusawa et al. (2005) "Determination of log P-o/w for Catechins and their Isomers, Oligomers, and Other Organic Compounds by Stationary Phase Controlled High Speed Countercurrent Chromatography," *J. Liq. Chromatogr. Relat. Technol.* 28:2819-2834.

Shinomiya et al. (Mar. 2006) "Countercurrent Chromatographic Separation f Biotic Compounds with Extremely Hydrophilic Organic-Aqueous Two Phase Solvent Systems and Organic-Aqueous Three-Phase Solvent Systems," *J. Liq. Chromatogr. Relat. Technol.* 29(5):733-750.

Vallat et al. (1990) "Centrifugal Countercurrent Chromatography, a Promising Means of Measuring Partition-Coefficients," *J. Chromatogr.* 504:411-419.

Vidal et al. (2004) "Fractionation of Grape Anthocyanin Classes Using Multilayer Coil Countercurrent Chromatography with Step Gradient Elution," *J. Agric. Food Chem.* 52:713-719.

Zanatta et al. (2005) "Determination of Anthocyanins from Camu-Camu (*Myrciaria dubia*) by HPLC-PDA, HPLC-MS, and NMR," *J. Agric. Food Chem.* 53-9531-9535.

* cited by examiner

Solvent System Map

| $K_D$ intervals | $0 \le K_D < 0.0625$ | $0.0625 \le K_D < 0.125$ | $0.125 \le K_D < 0.25$ | $0.25 \le K_D < 0.5$ | $0.5 \le K_D < 1$ | $1 \le K_D < 2$ | $2 \le K_D < 4$ | $4 \le K_D < 8$ | $8 < K_D < 16$ | $16 \le K_D < 32$ | $32 \le K_D < \infty$ |
|---|---|---|---|---|---|---|---|---|---|---|---|
| 10:0:10 | rTXH | | | D | CG | | | | | | FVAUMNE RZQOIYb |
| 8:2:10 | r | T | XH | | | DC | | G | | | FVAUMNE RZQOIYb |
| 6:4:10 | r | | | TXH | | DC | | G | | | FVAUMNE RZQOIYb |
| 4:6:10 | r | | | | TXH | D | C | G | | | FVAUMNE RZQOIYb |
| 2:8:10 | r | | | | TXH | D | C | G | | | FVAUMNE RZQOIYb |
| 0:10:10 | r | | | | TXH | D | C | G | | F | VAUMNER ZQOIYb |

EBuWat / Sweet Spot

Fig. 3 a) EBuWat

*polar* r T X H D C G V A F U M N E R Z Q O I Y b *nonpolar* b) *ter*AcWat r T X H C D G R V A F U M Z Q N E O I Y b c) *ter*AcWat 6:4:10 r T X H C D G R V A F U M Z Q N E O I Y b d) H*ter*AcWat 4:6:4:6 r T X H C D G R F V A U Q M Z N E O I Y b

Fig. 4

Solvent System Map — terAcWat

| $K_D$ intervals | $0 \leq K_D < 0.0625$ | $0.0625 \leq K_D < 0.125$ | $0.125 \leq K_D < 0.25$ | $0.25 \leq K_D < 0.5$ | $0.5 \leq K_D < 1$ | $1 \leq K_D < 2$ | $2 \leq K_D < 4$ | $4 \leq K_D < 8$ | $8 \leq K_D < 16$ | $16 \leq K_D < 32$ | $32 \leq K_D < \infty$ |
|---|---|---|---|---|---|---|---|---|---|---|---|
| 10:0:10 | rTXH | | CDG | | | | | | RVA | UFM | ZQNE OIYb |
| 8:2:10 | rTXH | | C | DG | | | | R | VA | UFM | ZQNE OIYb |
| 7:3:10 | rTXH | | | CD | G | | | R | VA | UFM | ZQNE OIYb |
| 6:4:10 | rTXH | | | | CDG | | | R | VA | UFM | ZQNE OIYb |
| 5:5:10 | rTXH | | | | CD | G | | R | VA | UFM | ZQNE OIYb |
| 4:6:10 | r | | T | XH | CD | G | R | V | AUF | MZ | QNEOI Yb |

Sweet Spot

Fig. 6

Solvent System Map — HterAcWat

| $K_D$ intervals | $0 \leq K_D < 0.0625$ | $0.0625 \leq K_D < 0.125$ | $0.125 \leq K_D < 0.25$ | $0.25 \leq K_D < 0.5$ | $0.5 \leq K_D < 1$ | $1 \leq K_D < 2$ | $2 \leq K_D < 4$ | $4 \leq K_D < 8$ | $8 \leq K_D < 16$ | $16 \leq K_D < 32$ | $32 \leq K_D < \infty$ |
|---|---|---|---|---|---|---|---|---|---|---|---|
| 10:0:10:0 | rTXHGDC RFVUAQN EMZ | | | O | I | | | | | Y | b |
| 8:2:8:2 | rTXHGDC RFVUAQN | E | MZ | | O | | I | | | | Yb |
| | | | | | | | | | | | |
| 4:6:5:5 | rTXH | | DCG | | | RF | AVU | Q | M | ZN | E OIYb |
| 4:6:4:6 | rTXH | | DCG | | | RF | AVU | Q | M | ZN | E OIYb |
| 3:7:3:7 | rTXH | | DC | G | | | RF | AVU | M | ZQ | NE OIYb |
| 2:8:2:8 | rTXH | | DC | | G | | | RA | FVU | M | ZQNE OIYb |
| 0:10:0:10 | rTXH | | DCG | | | | | | RAV | FUM | ZQNE OIYb |

Sweet Spot

Fig. 9

SELECTION AND RATIONAL DEVELOPMENT OF SOLVENT SYSTEMS IN COUNTER-CURRENT CHROMATOGRAPH

CROSS-REFERENCE TO RELATED APPLICATIONS

This application claims the benefit of U.S. provisional application Ser. No. 60/853,079, filed Oct. 20, 2006, which is incorporated by reference herein in its entirety.

BACKGROUND OF THE INVENTION

Counter-current chromatography (CCC) is gaining popularity as a viable separation technique, particularly in natural products chemistry. For example, high-speed counter-current chromatography (HSCCC) and centrifugal partition chromatography (CPC) have increasingly been used to isolate and purify a multitude of natural products [1-14]. Despite its indisputable worth, CCC has often been passed over for other chromatographic techniques. The lack of a clear method for Characterizing the properties and comparing the relative merits of the many possible biphasic solvent systems that might be used for CCC appears to be a major drawback to the use of CCC separations. The choice of solvent system for CCC separations is of utmost importance to the successful use of the method. Compared to the far more popular solid-support chromatography, the selection of CCC solvent systems is significantly more challenging because it is equivalent to simultaneously choosing both the column and the eluant.

Many CCC solvent systems have been proposed, studied and successfully employed over the years as reviewed in several articles [15-19]. Even though CCC is a high-resolution chromatographic method, it will not separate desired target analytes in any appreciable way unless the solvent system has been chosen very carefully. There is a window of opportunity present in CCC separations that is related to the $K_D$ value of a given chemical species, typically a molecule, in a particular solvent system. The distribution constant, $K_D$, for a given chemical species can be expressed as the concentration of that chemical species in the stationary phase divided by the concentration of the chemical species in the mobile phase. A solvent system, where the $K_D$ value of a particular chemical species is close to one, is generally considered to be the ideal system for separating that particular chemical species with optimal resolution. From this perspective, the varied chemical constituents of a particular mixture can be schematically arrayed along a polarity continuum as a function of $K_D$ of the chemical constituents in a given solvent system. In such an array for a given solvent system, CCC separation targets an interval of the polarity continuum, called the "sweet spot" of optimal resolution [20], and the solvent system can be used in CCC to separate the chemical constituents that fall within this sweet spot with high resolution. In order to represent the position of the sweet spot in a polarity continuum, two different schematics have been developed.

Use of a CCC technique called elution-extrusion (EECCC) [21-24] has the effect of maximizing the width of the sweet spot for a given solvent system and, at the same time, minimizing run times. Under elution-extrusion conditions, compounds already separated in the column are eluted (ideally) without further change in resolution. The $K_D$ value of each chemical species can be calculated from its retention time and the appropriate parameters, as is known in the art. EECCC chromatograms of complex mixtures wherein the mixture consistutents exhibit a with a wide range of polarities tend to have a cluster of chemical species eluted near the void volume ($0<K_D<0.25$) and another cluster near the end of the run where the last component(s) are eluted ($16<K_D<\infty$ in this example). In between the two extremes lies the sweet spot ($0.25 \leq K_D \leq 16$) where optimal resolution of compounds is observed.

Biphasic solvent systems for CCC applications have traditionally been organized as solvent families that are comprised of the same solvents mixed in varying proportions. Common solvent families are hexane/ethyl acetate/methanol/water (HEMWat), chloroform/methanol/water (ChMWat), and heptane/ethyl acetate/methanol/water (the "Arizona" family) [25]. Solvent system families provide a methodical means of searching for a particular solvent system that predicts a reasonable $K_D$ value for the target compound(s) in a CCC separation. For example, if a relatively high concentration of a particular chemical species is determined to be present in the upper phase of the HEMWat system 0 (see Table 1, where system 0 contains equal relative proportions of the four solvents of the system family), the $K_D$ value of that chemical species will likely be brought closer to 1 (an equal concentration of the compound in both phases) by decreasing the ratios of ethyl acetate to hexane and/or water to methanol as in a system such as HEMWat–3. In this way, once a particular solvent system family member has been tested as portal to the solvent system family, there exists a methodical way to modifying the solvent system to seek one that will exhibit an optimal $K_D$ value for the target chemical species.

A factor that distinguishes one solvent system family from another is the polarity range of chemical species for which the solvent system family may be optimized. For example, the HEMWat solvent system family is generally considered to separate compounds of lipophilic to moderate polarity, while the ethyl acetate/n-butanol/water is a solvent system family that is likely to separate compounds of moderate to hydrophilic polarity. As the aforementioned example suggests, there may be considerable overlap of polarity ranges between solvent system families that introduces a degree of empiricism to the solvent system selection process.

It is important to note that in liquid/liquid chromatography separation is driven by the relative solubilities of the analytes in the two different solvent layers, and not strictly by their relative polarities. In fact, CCC has been shown to be an excellent technique for separating homologues with very similar polarities [26, 27]. However, the concept of relative polarity does provide a convenient framework with which to represent the separation potential of organic compounds.

Hitherto, no standard method existed to evaluate solvent system or solvent system family performance and, therefore, the solvent system selection process has been essentially empirical in nature.

The present invention provides a systematic way to evaluate solvent system performance and make rational selections of one or more solvent systems for the separation of constituents (unknown or known) in a given mixture.

SUMMARY OF THE INVENTION

The invention provides a method for mapping the polarity range of a solvent system or a solvent system family. The mapping information provided can specifically be employed for selection of solvents systems and solvent families for separation of components of target mixtures. More generally, mapping information can be employed to provide polarity classification of a given solvent system for CCC applications, and to determine which solvent system in a given solvent family is a good starting point for entry for systematic variation of the relative proportions of solvent system component solvents in order to achieve enhanced separations. The mapping method can also be employed to systematically formulate new solvent systems and new solvent system families, such as the HterAcWat solvent family. The mapping method can further be employed to assess and select columns (the stationary phase of the countercurrent solvent system).

The mapping method can also generally be used to assess relative performance of different CCC and CPC instruments, for calibration of separations made in different instruments, for quality control and troubleshooting for instrumental problems.

In a specific embodiment, mapping of a solvent system or solvent family comprises (1) providing a reference mixture of reference components (b) selecting a solvent system or a plurality of solvent systems of a solvent system family and (c) determining the distribution constant ($K_D$) for each reference component in the selected solvent system or in each selected solvent system of the solvent system family. The $K_D$ of the components of the reference mixture are determined employing CCC and more specifically employing elution-extrusion CCC (EECCC). In a more specific embodiment, the sweet spot of one or more solvent systems is mapped with the $K_D$s of the reference components of the reference mixture.

When a solvent system family is mapped the plurality of solvent systems selected spans the range of relative proportions of the solvent components of the solvent system family and is representative of the family. In a specific embodiment, the solvent systems that are mapped are biphasic solvent systems.

Most generally the reference mixture comprises at least three structurally distinct chemical species of different polarity and different molecular mass and the mixture comprises at least one hydrophilic component and at least one lipophilic component. The reference mixture can contain four or more, 10 or more or 20 or more reference components. In specific embodiments, the components of the reference mixture are natural products. Specific useful reference mixtures are provided herein below.

The mapping method employing a reference mixture of known components can further be combined with a qualitative or quantitative method which compares the partition functions ($K_D$) of one or more components of a target mixture with one or more or two or more of the components of the reference mixture. This combined method allows selection of a solvent system or solvent system family that can be expected to separate the one or more components of the target system from other components in the target mixture. The selection is based on matching $K_D$s of one or more unknown components to those of one or more reference compounds which have $K_D$s with in the sweet spot ($K_D$ ranging from 0.25 to 16) in the a given solvent family or system. Target components which are found to qualitatively or quantitatively match $K_D$s of the reference components which are separated in CCC by a given solvent system are expected to also be separated by that solvent system.

In a specific embodiment the invention provides a method for selecting a solvent system or solvent system family for use in separation of one or more chemical components of a mixture by CCC. The method comprises the steps of mapping the polarity range of the solvent system or solvent systems as described above employing a reference mixture as described above and determining which of the reference components that have $K_D$ ranging from 0.25 to 16 in the one or more mapped solvent systems have relative $K_D$s which match the components of the target system which are to be separated. Matching of relative polarities or $K_D$s involves determination of relative polarities or KDs employing a method other than CCC. In particular, qualitative or quantitative determination of relative polarities and/or $K_D$s can be determined using thin layer chromatography, liquid chromatography (TLC), such as HPLC, or gas chromatography. In a specific embodiment, relative $K_D$s can be determined by TLC in an appropriate solvent. Relative $K_D$s are determined by measuring relative Rf values employing TLC. The solvent or solvent system used for TLC can be one or more of the solvents of a mapped solvent system, but need not be. The solvent or solvent system used must provide a separation of the target components of interest and the reference components to be compared. In specific embodiments, a match of relative Rfs is defined by relative Rf values between 3 and 0.33. In a specific embodiment, the method can be employed to select a solvent system of a solvent system family selected from the group consisting of HEMWat, EBuWat, terAcWat, and HterAcWat. In specific embodiments, the solvent system selected is a biphasic solvent system.

In a specific embodiment, the invention provides a new solvent system family in which the solvent systems are a mixture of hexane, t-butyl methylether, acetonitrile and water. The solvent system family contains both biphasic and three-phase systems which can be sued in CCC. Biphasic solvent systems are preferred for use in CCC. In particular embodiments, the invention provides methods for carrying out CCC employing a solvent system which is a mixture of hexane, t-butyl methylether, acetonitrile and water in which the relative proportions of solvent components (by volume) of hexane:t-butyl methylether:acetonitrile:water range from 9:1:9:1 to 1:9:1:9. In another embodiment, the solvent system is a mixture of hexane:t-butyl methylether:acetonitrile:water ranging in volume proportion from to 4:6:5:5 to 1:9:1:9. This solvent system is particularly useful for the separation of natural products, such as those contained in plant extracts.

Additional aspects of the invention will be apparent on consideration of the drawings, the detailed description and the examples.

BRIEF DESCRIPTION OF THE DRAWINGS

FIG. 3. Is a representational map of the relative $K_D$ values for GUESSmix components in the six ethyl acetate/n-butanol/water (EBuWat) solvent systems.

FIG. 4. Is a schematic representations of the GUESSmix compounds in their respective order of elution in different solvent system families (a & b) and solvent systems (c & d). The compounds in the gray box eluted in the sweet spot defined as $0.25 \leq K_D \leq 16$.

FIG. 6. Is a representational map of the relative KD values for GUESSmix compounds in six t-butylmethylether/acetonitrile/water (terAcWat) solvent systems.

FIG. 9. Is a representational map of the relative $K_D$ values for GUESSmix compounds in seven hexane/t-butylmethylether/acetonitrile/water (HterAcWat) solvent systems.

DETAILED DESCRIPTION OF THE INVENTION

Figure 1:
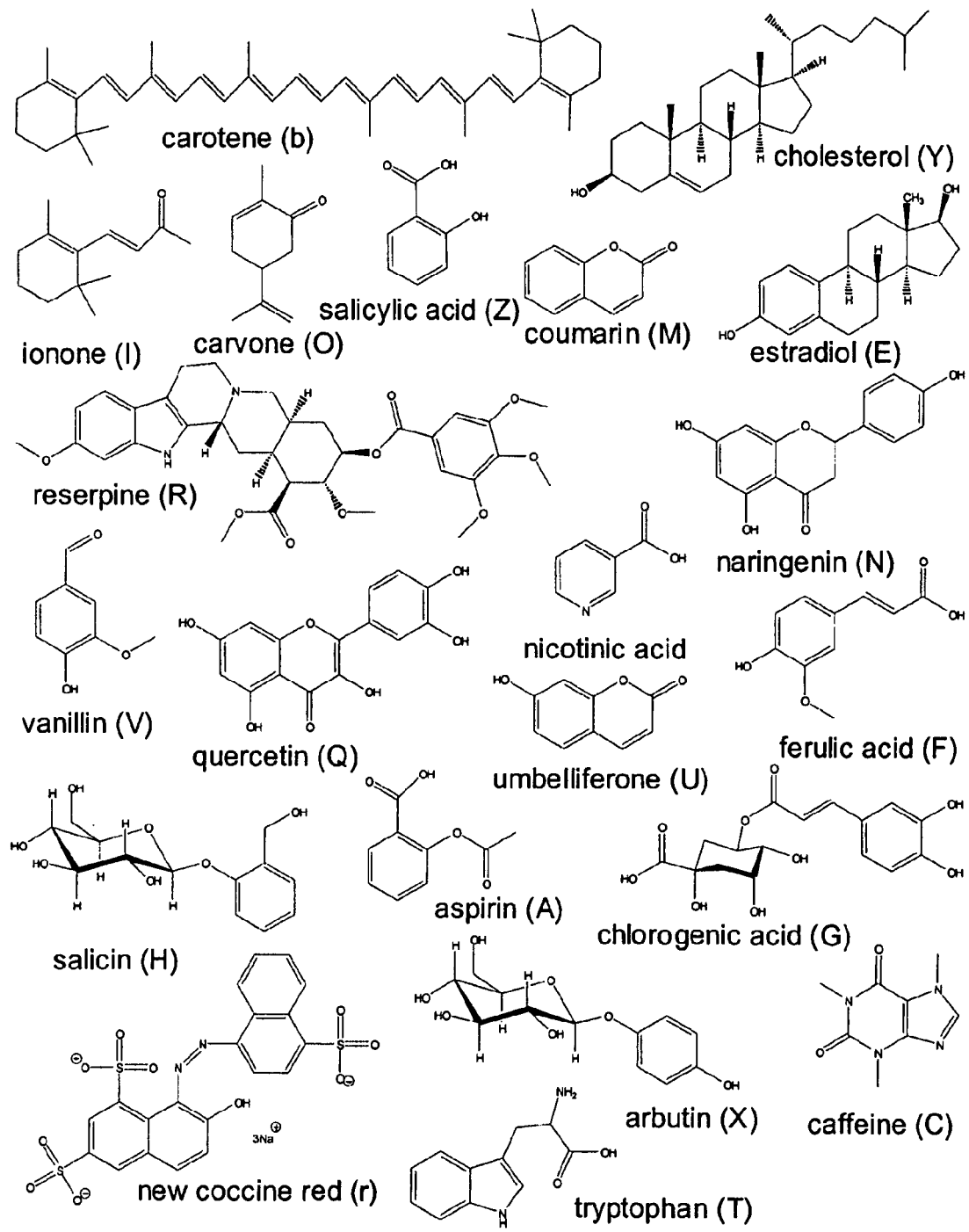
FIG. 1 provides the chemical structures of 21 components of the GUESSmix reference standard which is an exemplary mixture of reference natural products for use in the methods of this invention for mapping the polarity of one or more solvent systems. The one-letter abbreviations of the components are also provided.
Figure 2:
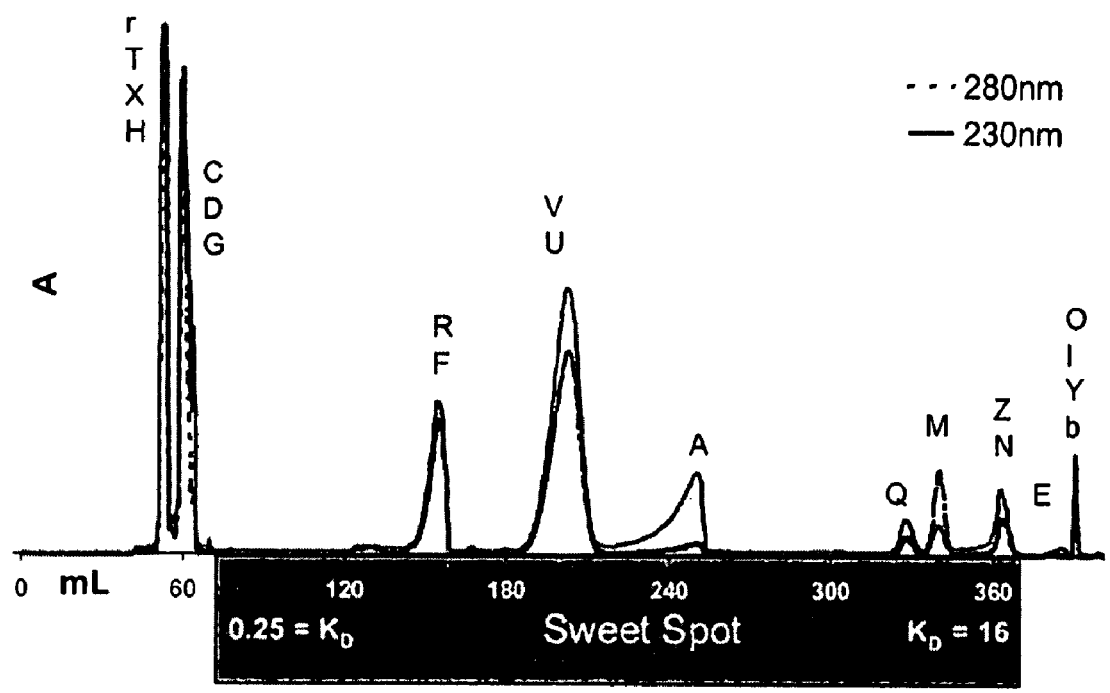
FIG. 2. Is a plot illustrating HSCCC separation of GUESSmix components in hexane/t-butylmethylether/acetonitrile/water 4:6:4:6 (Table 1). The lower aqueous phase was mobile with a flow rate of 1 mL/min from head-to-tail. The column exhibited a stationary phase retention volume ratio of 0.60. Extrusion was begun at 314 mL. KD values of 0.25, 1, and 16 were calculated to be at 66, 120, and 367 mL respectively.

Countercurrent chromatography (CCC) is a separation technique that distributes analytes between two immiscible liquid phases in order to effectuate their separation. The term CCC is used broadly herein to refer to countercurrent separation methods including [high-speed] countercurrent chromatography ([HS]CCC) and [centrifugal]partition chromatography ([C]PC). The absence of a liquid/solid or gas/liquid interface allows for the maximizing of surface interactions between the two chromatographic phases through continuous mixing and settling. For this reason, CCC is a high-resolution separation technique, capable of fractionating complex mixtures under very mild conditions, and only based on their relative solubility in the two immiscible phases. CCC has the added advantage that it can be reproducibly scaled up by simply increasing the size of the column.[4]

Due to the exclusive involvement of liquids (solvents), it is widely accepted that CCC permits the complete recovery of all analytes introduced to the column. The retention volume of an analyte follows the classical elution equation (1).

$$V_R = V_M + KV_S \quad (1)$$

The ratio of the analyte concentration in the stationary phase to its concentration in the mobile phase determines the analyte's distribution constant, $K_D$. The equation shows the relationship between the K value and the experimentally measurable parameters of retention volume ($V_R$), mobile phase volume ($V_M$), and stationary phase volume ($V_S$). However, if a column is eluted only with mobile phase, it will theoretically take an infinite amount of time for an analyte that is exclusively soluble in the stationary phase ($K=\infty$) to exit the column.

In practice, one way of overcoming this limitation and to ensure that all the analytes are recovered is to completely extrude the column contents (both stationary and mobile phase) at a defined point of the elution stage of the chromatography. This method has recently been developed by Berthod and coworkers [22], who described the basic theory and introduced the term of elution-extrusion CCC (EECCC). Extrusion of the stationary phase is achieved by switching the supply of flowing liquid from the mobile phase to the originally stationary phase, while maintaining the centrifugal force through continued rotation (conditions found in modern CCC instrumentation). The calculation of $K_D$ values in EECCC chromatograms can be performed by applying two equations. During the classical mode (CM) elution stage, the following equation (2) describes the K value:

$$K = (V_R - V_M)/V_S \quad (2)$$

Upon initiating extrusion at volume $V_{CM}$ (classical mode elution volume) by switching the liquid phase supply, elution continues to occur for the volume of the mobile phase $V_M$. Thus, equation (2) yields the $K_D$ values of all those chemical species that actually elute, which occurs during the volume $V_{CM} + V_M$. In the subsequent extrusion stage, which is characterized by the effluent being exclusively the originally stationary phase, $K_D$ values are calculated by the following equation (3).

$$K = V_{CM}/(V_{CM} + V_C - V_R) \quad (3)$$

The point at which extrusion is begun can be adjusted to optimize the resolution of target analytes in a minimum amount of time. When $V_R$ is equal to $V_{CM} + V_C$ ($V_C$ is the total volume of the column), all analytes will have exited the column. The elution-extrusion concept, therefore, allows $K_D$ values to be calculated for all analytes, including those with $K_D$ values approaching infinity.

The invention is based in part on the use of a reference mixture, preferably a mixture of natural product, to evaluate solvent system performance, by mapping the polarity range of chemical species that can reasonably be expected to be separated by the solvent system. The mapping of a solvent system is performed using the reference mixture and determining by CCC the $K_D$ of reference components using the solvent system. A solvent system family can be likewise mapped by selecting a set of representative solvent systems in the solvent family that extend over the composition range of the solvent family (see: Tables 1, 3-5, for exemplary representative solvent systems that span the composition range of a given solvent family). It will be appreciated that a solvent system family can comprises a practically unlimited number of solvent systems of differing composition. Mapping of the solvent family does not require mapping of all possible members of the solvent family, it can be accomplished by mapping of representative solvent systems in the family.

It is of particular use to determine in a given solvent system which reference components of the reference mixture have $K_D$ which are I the sweet spot of CCC separation. This is generally the $K_D$ range from 0.25 to about 16 and more preferably is the $K_D$ range from 0.4 to 2.5. Components having $K_D$ in these ranges in a given solvent system are reasonably expected to be separated by CCC in that solvent system.

A reference mixture useful in the methods of this invention contains three or more components at least one of which is lipophilic and one of which is hydrophilic. Particularly for selection of solvent systems for natural product separations, it is preferred that the reference mixture comprises natural products. Preferred mixtures contain four or more, ten or more or twenty or more components. The components span a range of polarities, structures and molecular mass. However, all components are small molecules with molecular mass less than 2000 amu. The reference mixture preferably contains neutral as well as acidic and basic components. The components also preferably have varied functional groups. For convenience the components are preferably commercially available. Additionally, the components should be readily detectable, e.g., they should be UV active.

The term natural product is used broadly herein to encompass any organic molecules derived from a terrestrial or marine organism. Natural products useful in reference mixtures of this invention include; sugars or glycosides, amino acids, polyketides (acetates), phenylpropanoids, terpenoids or isoprenoids as well as components of mixed natural origin. The exemplified Q.U.E.S.S.mix contains natural products that are or are derived from sugars (e.g., salicin), amino acids (e.g., tryptophan), terpenoids (e.g., ione, carvone, carotene, cholesterol, estradiol,), phneylpropanoids (e.g., chlorogenic acid, ferulic acid, umbelliferone) and polyketides (e.g., vanillin, and aspirin) as well as components of mixed origin (naringenin and caffeine).

An exemplary preferred reference mixture is a 21 component mixture that is herein called the GUESSmix. The chemical structures of the GUESSmix reference standards are shown in FIG. 1 and their selected attributes are provided in Table 2. The GUESS-mix was previously developed [20] to provide a TLC-based method for the Generally Useful Estimation of Solvent Systems (G.U.E.S.S.) in CCC.

In another embodiment, a truncated GUESSmix can be employed which has a total of 12 components: carotene, carvone, estradiol, salicyclic acid, naringenin, coumarin, umbelliferone, quercitin, ferulic acid, vanillin, caffeine and new coccine red. In these exemplary GUESSmix reference mixtures, carotene functions as a lipophilic marker and new coccine red (which is not itself a natural product) functions as a hydrophilic marker.

The polarity of a given solvent system is mapped by performing CCC separations and determining $K_D$s of the components of a selected reference mixture. Preferably initial mapping is performed employing reference mixtures having 12 or more or 20 or more components as described herein. The resolution of the polarity mapping of a given solvent system can be increased or decreased by respectively increasing or decreasing the number of reference components employed in the mapping. For example, if it is desired to provide a higher resolution map of a particular portion of interest in the sweet spot of a given solvent system, additional reference components can be added to the reference mixture which have polarity similar to those reference components that were found to have $K_D$s in that portion of interest. For example, in the EBuWat solvent system of FIG. 3, the sweet spot region between $K_D$ of 1 to 2 may be mapped with higher resolution by adding additional reference components similar in polarity and structure to nicotinic acid (D).

A standard method of solvent system analysis preferably (1) comparison of the sweet spot polarity range of solvent systems within a family; (2) identification of the portal solvent system that is most representative of a solvent system family; (3) comparison of the overall sweet spot polarity ranges and changes in order of elution between solvent system families; and (4) development and evaluation of CCC solvent system families with desired performance characteristics. The methods of this invention employing the reference mixtures as described herein facilitate each of (1) through (4).

Exemplary applications of polarity mapping using a natural products reference mixture to solvent system analysis are provided herein. For example, polarity mapping can provide polarity classification of a given solvent system for CCC application. As will be seen based on mapping, the EBuWat solvent family is classified useful for separation of the more polar chemical species. The mapping method can also be used to determine which solvent system in a given solvent family is a good starting point for entry for systematic variation of the relative proportions of solvent system component solvents in order to achieve enhanced separations. Again for example in the EBuWat system the 4:6:10 (EBuWat+1), is selected as the best portal solvent system for the family. Most generally, this is the solvent system of the family in which the most components of the reference mixture are in the $K_D$ range 025 to 16.

The mapping method can be employed to systematically formulate new solvent families and systems as illustrated with the HterAcWat solvent family below. The mapping can also be employed to assess and select columns for CCC which represent the stationary phase of the countercurrent solvent system.

The information obtained by the mapping method of this invention, as illustrated in the solvent system maps provided herein, can generally be used to assess relative performance of different CCC and CPC instruments. Comparisons are made by comparing a reference mixture map of $K_D$'s, of at least three mixture components and preferably more than three mixture components, obtained with one instrument with an analogous map made with another instrument. Additional, the mapping information can be used for calibration of separations in different instruments, for quality control and troubleshooting for instrument problems. The mapping method employing a reference system of known components can further be combined with a qualitative or quantitative method which compares the partition functions of one or more unknown components of a target mixture with two or more of the components of the reference mixture. This combined method allows selection of a solvent system family or more specifically a solvent system that can be expected to separate the one or more unknown components from other components in the target mixture. The selection of a given solvent family or system is made based on matching the $K_D$s of one or more unknown components to those of one or more reference compounds which have $K_D$s with in the sweet spot ($K_D$ ranging from 0.25 to 16) in the solvent family or system. Unknowns which are found to qualitatively or quantitatively match $K_D$s of the reference components which are separated in CCC by a given solvent system are expected to also be separated by that solvent system. In general, any methodology that determines relative Kd values is suitable for use in this invention.

The matching of unknowns and reference components does not require determination of the $K_D$s of unknowns using CCC. The qualitative or quantitative comparison of reference and unknowns is performed by a method other than CCC, for example employing liquid column chromatography, including thin layer liquid chromatography and high performance liquid chromatography (HPLC) or variants of such techniques, or gas chromatography. While relative $K_D$ values of different components inn a solvent system can be assessed using the "shake-flask" method as known in the art [20]. The "shake-flask" method requires relative large amounts of the unknowns and is not practical for most applications. The determination of whether or not a given unknown matches a given reference component depends upon the comparison techniques employed.

In TLC, which is a preferred method, the relative Rf values of reference components and unknowns can be assessed to provide a comparison of $K_D$s. in TLC the target unknowns which match the reference components are those which are within an Rf range of 3 or less, more preferably between 2 and 0.5, and most preferably between 1.5 and 0.75 of the Rf of a reference component. In other words, a match is found when the relative Rf value, as determined by TLC in any appropriate solvent, of an unknown to a reference ranges is between 3 and 0.33 and is more preferably is between 2 and 0.5 or yet more preferably is between 1.25 and 0.75.

HPLC methods can also be used to obtain log P values which are correlated as is known in the art with HPLC retention times. Again a match between a component in a target mixture and a reference component is found when the ratio of HPLC retentions times of the reference to the target component range from 3 to 0.33. It is preferred that the ratio of retention times for determining a match range from 2 to 0.5 and yet more preferably that the ratio ranges from 1.25 to 0.75.

TLC, HPLC or other chromatographic method used for the comparison of $K_D$s is generally performed as understood in the art to obtain separation of the target components of interest. In particular it will be understood that for any type of chromatography that is used in this comparison that an accurate comparison is best obtained if the components that are compared (target and reference) are separated in the 20% to 80% retention window of the technique employed.

To assess the ability of a given solvent system to separate one or more unknowns in a target mixture, comparisons of relative polarities, $K_D$s or Rf values can be made with all or a selected subset of the reference components that have $K_D$s between 0.25 and 16 (the sweet spot) in that solvent system. In a specific embodiment, comparisons need only be made with two reference components with bracket the sweet spot of a given solvent systems (i.e., those reference components which exhibit the highest and the lowest $K_D$s that still are within the sweet spot). For example, assessment of solvent system appropriate for a large number of target mixtures could be made by TLC analysis of the unknowns compared to such sweet spot bracketing reference components.

A target mixture is a mixture of components which it is desired to separate. Target mixtures include among others, plant or animal tissue extracts, and fermentation cultures or extracts thereof of bacteria or other microorganisms, The EBuWat Family of Solvent Systems (Ethyl Acetate/n-Butanol/Water)

A solvent system family comprised of ethyl acetate/n-butanol/water (EBuWat) has been previously described in the CCC literature [15,16] and has enjoyed some application as the solvent system of choice for natural product isolations [28-32]. The EBuWat solvent system family (Table 3) targets compounds of moderate to hydrophilic polarity. The general organization of the solvent system family can be described as organic/organic modifier/water. In this case, the alcohol, n-butanol, is considered to be an organic modifier since it is miscible with ethyl acetate but only somewhat miscible with water.

FIG. 3 is a representational map of the relative $K_D$ values for the GUESSmix compounds in six EBuWat solvent systems. In general, $K_D$ increases as the ratio of n-butanol relative to ethyl acetate increases. However, compared to the overall polarity range of the GUESSmix compounds, there is a fairly limited range of $K_D$ values as the solvent proportions go from ethyl acetate/water 1:1 to n-butanol/water 1:1.

The overall range in polarity revealed by the GUESSmix in all six solvent systems can be illustrated by arranging the letter abbreviations for the compounds in their order of elution from hydrophilic (low $K_D$ values) to lipophilic (high $K_D$ values). A hydrophilic red dye, "r", is used to mark the end of the void volume, and a lipophilic orange dye, "b", is used to mark the end of extrusion. Those compounds that are present in the sweet spot in any one of the solvent system family members are represented by outlined letters. In the case of EBuWat, shown in FIG. 4a, the representation shows that the more polar members of the GUESSmix are likely to be present in the sweet spot.

Figure 5:
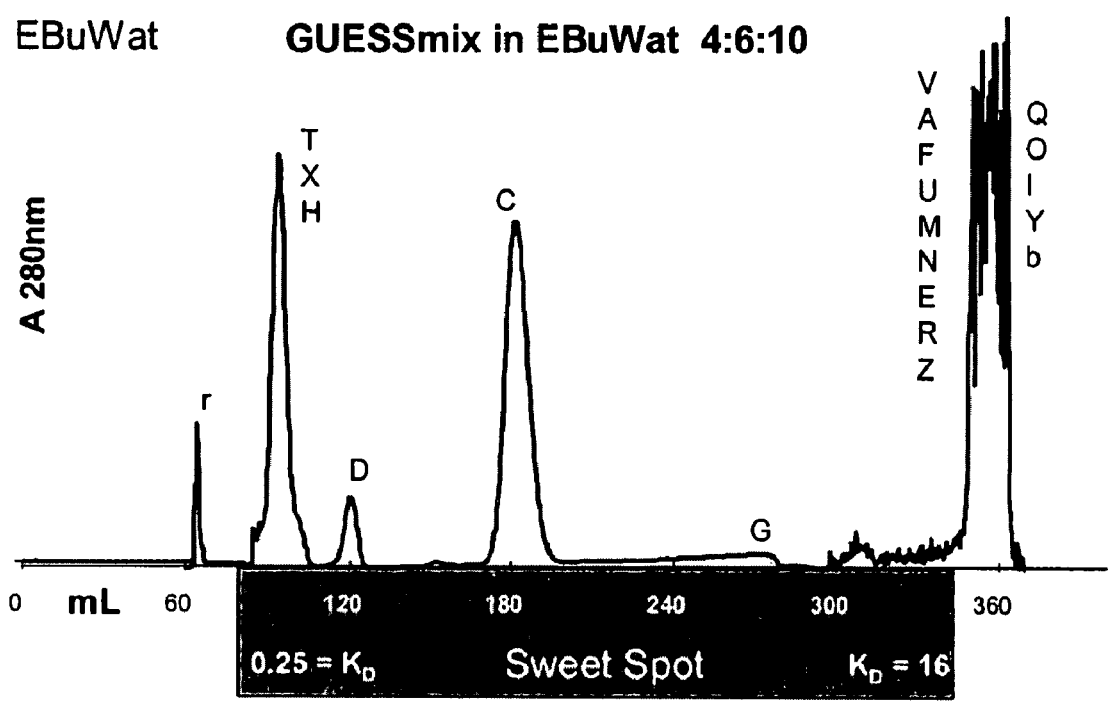
FIG. 5. is a plot illustrating HSCCC separation of GUESSmix compounds in ethyl acetate/n-butanol/water 4:6:10 (EBuWat+1). The lower aqueous phase was mobile with a flow rate of 1 mL/min from head-to-tail. The column exhibited a stationary phase retention volume ratio of 0.45. Extrusion was begun at 312 mL. KD values of 0.25, 1, and 16 were calculated to be at 80, 120, and 350 mL respectively.

From these results, the solvent system 4:6:10 (EBuWat+1), shown in FIG. 5, appears to be the best portal solvent system with which to enter this solvent system family. This means that if a compound mixture is tested with EBuWat+1 and the target compounds are not present in the sweet spot, it is unlikely that other EBuWat solvent systems will be able to resolve these compounds. However, if a compound mixture is tested with the EBuWat+1 and the target compound(s) are present in the sweet spot but not optimally resolved, it may be useful to try other members of the EBuWat solvent system family to better resolve these compounds. For example, arbutin (X) and tryptophan (T) have $K_D$ values of 0.56 and 0.56 in EBuWat+1 and 0.56 and 0.9 respectively in EBuWat+5.

The terAcWat Family of Solvent Systems (t-Butylmethylether/Acetonitrile/Water)

A solvent system family comprised of t-butylmethylether/acetonitrile/water (terAcWat) has previously been described in CCC literature (Table 4) [15,16]. The solvent t-butylmethylether has occasionally been used as a component of a CCC solvent system for natural product isolation [33-39].

Similar to the EBuWat solvent system family, the terAcWat solvent system family targets compounds of moderate to hydrophilic polarity. In contrast to the EBuWat solvent system family, the general organization of the terAcWat family can be described as organic/aqueous modifier/water. Here, acetonitrile is considered to be an aqueous modifier since it is immiscible with t-butylmethylether but miscible with water. The possible solvent proportions are limited in this solvent system family by the fact that increasing the proportion of acetonitrile relative to t-butylmethylether eventually results in a single-phase solvent system.

FIG. 6 is a representational map of the $K_D$ values for the GUESSmix compounds in six terAcWat solvent systems. In general, $K_D$ increases as the ratio of acetonitrile relative to t-butylmethylether increases. Similar to the EBuWat solvent system family, there is a fairly limited range of $K_D$ values for most of the GUESSmix compounds as the proportions change from t-butylmethylether/water 1:1 to terAcWat 4:6:10.

FIG. 4b shows that, in the case of the terAcWat family, the overall polarity range representation shows that the more polar members of the GUESSmix are likely to be present in the sweet spot. The order of elution and the range of polarity are similar to the EBuWat family previously described. However, reserpine (R), naringenin (N), and quercetin (Q) have changed their positions in the polarity continuum. In addition, the polarity range has shifted slightly towards the lipophilic end.

Figure 7:
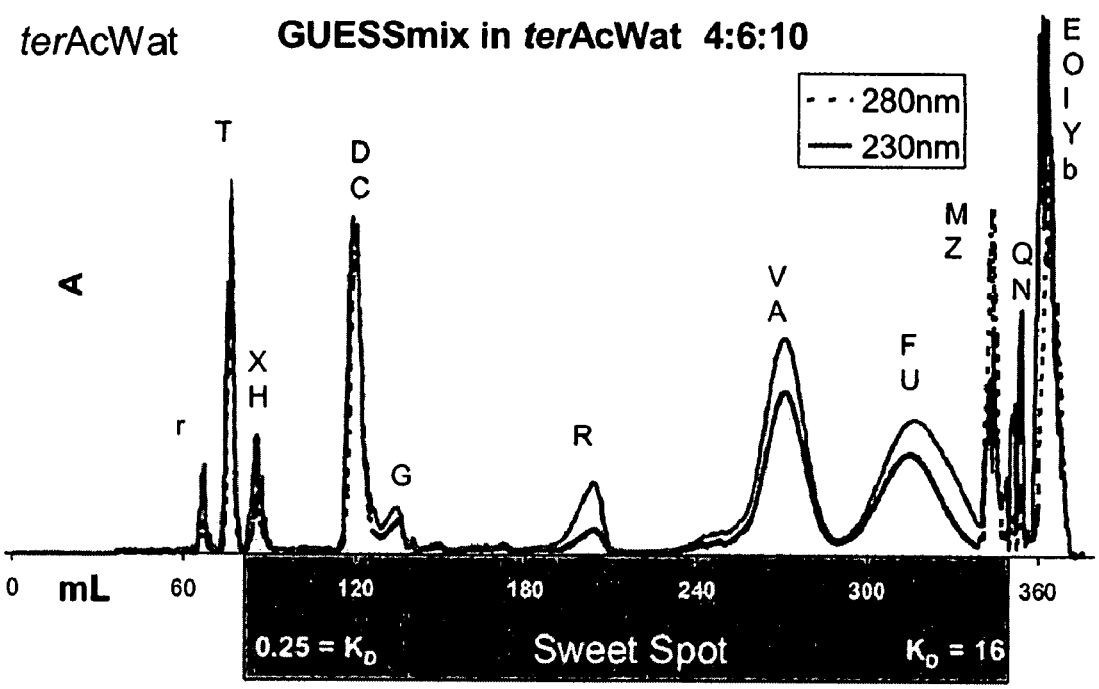
FIG. 7. is a plot illustrating HSCCC separation of GUESSmix compounds in t-butylmethylether/acetonitrile/water 4:6:10. The lower aqueous phase was mobile with a flow rate of 1 mL/min from head-to-tail. The column exhibited a stationary phase retention volume ratio of 0.44. Extrusion was begun at 335 mL. KD values of 0.25, 1, and 16 were calculated to be at 80, 120, and 356 mL respectively.

The solvent system 4:6:10 (terAcWat+1), shown in FIG. 7, appears to be the best portal solvent system for this solvent system family. In fact, the 4:6:10 sweet spot comprises all the compounds present in the sweet spots of other solvent systems in this family, as well as four that are not. However, all compounds are not at their optimal resolution in the 4:6:10 such as, caffeine (C) and nicotinic acid (D) which have $K_D$ values of 0.96 and 0.96 in terAcWat+1 and 0.24 and 0.31 in terAcWat-3 respectively.

Figure 8:
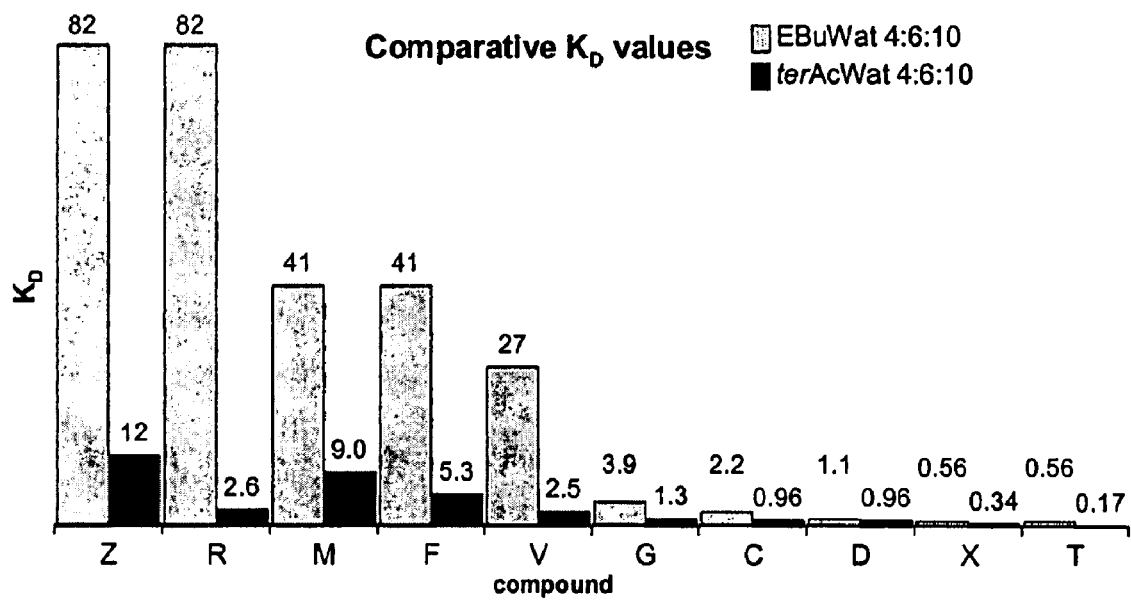
FIG. 8. Is a graph providing $K_D$ values for ten GUESSmix compounds in ethyl acetate/n-butanol/water 4:6:10 (EBuWat+1) and t-butylmethylether/acetonitrile/water 4:6:10 (terAcWat+1) solvent systems.

Based on the chromatographic behavior of the GUESSmix compounds, the rational comparison between the solvent system families of EBuWat and terAcWat becomes possible. Despite their polarity ranges exhibiting considerable overlap, there are important differences between the two families. For example, the $K_D$ values for individual compounds in EBuWat+1 and terBAcWat+1 vary significantly, as shown in FIG. 8.

Moreover, even though the two solvent systems have similar overall polarity ranges, they differ significantly in their ability to separate certain compound pairs. For example, the pair of caffeine (C) and nicotinic acid (D) is inseparable with the terAcWat+1 solvent system, but is fully resolved in EBuWat+1. On the other hand, the compound pair of coumarin (M) and ferulic acid (F) almost co-elutes in EBuWat+1, but is separated in terAcWat+1.

The HterAcWat Family of Solvent Systems (Hexane/t-Butylmethylether/Acetonitrile/Water)

In order to adjust the range of t-butylmethylether/acetonitrile/water solvent system family to include more lipophilic compounds, a solvent system family was developed by adding hexane as a fourth solvent (Table 5). The organization scheme of this new solvent system family follows the scheme: organic/organic modifier/aqueous modifier/water.

The fact that some relative proportions yielded three-phase solvent systems is an intriguing characteristic of this family. Recently, three-phase solvent systems have been prepared, described, and employed in the separation of natural products [40-42]. However, due to poor stationary phase retention volume ratios, these solvent systems were not included in this study.

FIG. 9 is a representational map of the relative $K_D$ values for the GUESSmix compounds in seven hexane/t-butylmethylether/acetonitrile/water (HterAcWat) solvent systems. In general, $K_D$ increases as the ratios of t-butylmethylether to hexane and/or water to acetonitrile increase.

FIG. 9 shows a dramatic change in $K_D$ values for some of the GUESSmix compounds between HterAcWat 8:2:8:2 (HterAcWat−6) and 4:6:5:5 (HterAcWat+1) as a result of a shift in the sweet spot from lipophilic to moderate polarity. Similar to the previous solvent system family, the condition for two distinct phases limits the possible effectiveness of the solvent system family.

FIGS. 4c and 4d show that the addition of hexane to t-butylmethylether/acetonitrile/water shifted the sweet spot towards the lipophilic GUESSmix compounds. It also widened the overall sweet spot polarity range of the solvent system family reminiscent of polarity range previously reported for the HEMWat solvent system family [20]. In addition, the inclusion of hexane in the solvent system changed the order of elution for several compounds, especially within and around the sweet spot. The GUESSmix, previously developed as a TLC-based tool for targeted identification of CCC solvent systems, is also fit for the purpose of providing a systematic method of solvent system analysis by mapping the sweet spot polarity range of solvent systems within a solvent system family. It was demonstrated that the sweet spot polarity range varies with the polarity of compounds and number of compounds included as the relative ratios of solvents were changed.

An overall sweet spot polarity range for a given solvent system family can be described to include all GUESSmix compounds that were in the sweet spot in at least one solvent system member of the family. This provides a reference point for the comparison of solvent system families and their rational development. The GUESSmix provides a systematic method of solvent system analysis to compare the sweet spot polarity ranges and changes in order of elution between solvent system families. This would have particular influence when fractions collected in one CCC solvent system are re-chromatographed in a second CCC solvent system.

In addition, based on the separation of the GUESSmix standards and considering all the solvent systems in a single family, one portal solvent system can be identified that offers a best first solvent system choice for an initial test run of a unknown sample. Much like the concept of the largest common denominator, the portal system is represented by the system that performs relatively best on the majority of GUESSmix standards in the sweet spot.

Finally, the GUESSmix provides for a logical method of developing and evaluating CCC solvent system families with desired performance characteristics. While phase limitations are an important consideration when evaluating overall solvent system family performance, mapping the sweet spot of the GUESSmix standards proves to be fit for the purpose of rational design of CCC solvent families.

THE EXAMPLES

Instrumentation

High-speed counter-current chromatography was carried out using a J-type instrument (Model CCC-1000; Pharma-Tech Research, Baltimore, Md., USA) containing a self-balancing three-coil centrifuge rotor equipped with 3×40 mL columns, the internal diameter of PTFE tubing was 1.6 mm. The revolution radius of the distance between the holder axis and central axis of the centrifuge (R) was 7.5 cm. The $\beta_r$ value varied from 0.47 at the internal terminal to 0.73 at the external terminal ($\beta_r$=r/R where r is the distance from the coil to the holder shaft). The HSCCC system was equipped with a Lab-Alliance Series III digital single-piston solvent pump, a Shimadzu SPD-10A UV-Vis detector with preparative flow cell, a Cole-Parmer modular paperless recorder model 80807-00, and a ISCO Lab Alliance, Foxy Jr. fraction collector.

Analytical TLC was performed at room temperature on Alugram precoated 0.20 mm thick silica gel G/UV$_{254}$ aluminum plates (20×20 cm; Macherey-Nagel, Düren, Germany). Plates were cut to 9.5 cm length and various widths before spotting. TLC experiments were carried out in duplicate. Plates were dipped in the general-purpose reagent p-anisaldehyde/sulfuric acid/acetic acid 1/1/48, drained, and heated on a Camag TLC Plate Heater III at 95° C. for about 5 minutes. All TLC chromatograms were scanned for digital preservation at 150 dpi with a Canon CanoScan N670U scanner.

Solvents and Reagents

All solvents were HPLC grade from Fisher Scientific (Hampton, N.H., USA) or Sigma-Aldrich (St. Louis, Mo., USA). Chemicals were purchased from Sigma-Aldrich.

High-Speed Counter-Current Chromatography (HSCCC)

GUESSmix samples were prepared as previously described in the form of a stock solution with a final concentration of approximately 0.1 g/mL of combined compounds [22]. The stock solution was stored at −30° C. and warmed to room temperature before use.

In order to prepare the GUESSmix for a chromatographic run, a 2.2 mL of the stock solution was removed and dried under forced air. The resulting residue was readied for HSCCC injection by suspension in equal volumes of upper and lower phase of the appropriate solvent system. The biphasic mixture of GUESSmix compounds was then filtered and loaded into a 2 mL sample loop.

All solvent systems were thoroughly mixed, vented and allowed to separate into two distinct phases before use. The HSCCC tubing was first filled with the (organic) stationary phase with no rotation. Then the coils were rotated 1200 rpm as the (aqueous) mobile phase was pumped at a flow rate of 1 mL/min from head-to-tail. In order to observe the stationary phase retention volume ratio in the column, the resulting effluent was collected in a graduated cylinder. When the volumes of the two phases of the eluant were approximately equal, the hydrodynamic equilibrium was considered to be established. To begin the run, the GUESSmix sample was injected on the column. A UV-Vis detector monitored the eluant, and all fractions were collected at 3 min/tube. After about two 240 mL of mobile phase had eluted from the column, organic phase was pumped into the column while the centrifuge was left running. Extrusion was determined to begin when all the mobile (aqueous) phase had exited the column. The run was stopped after the lipophilic marker compound, β-carotene, eluted from the column (120 mL after pumping the organic phase had begun). The collected fractions were reduced in volume and TLC performed to corroborate the UV-Vis data.

Solvent System Formulations

Solvent systems were formulated by mixing independently measured volumes of HPLC grade solvents. The final volumes were less than the sum of the component solvents due to mixing effects. The ratio of final volumes of upper and lower phases varied by solvent system formulation. No attempt was made to influence the pH of the final solvent system. Addition of acids, bases, and/or buffers would significantly alter the performance of the solvent system.

Solvent System Family Abbreviations

Abbreviated names for solvent system families are used in this work, taking into account solvent abbreviations that have been used previously: Ch=chloroform, E=ethyl acetate, H=hexane, M=methanol, and Wat=water. As a result, cumbersome solvent system combinations can be written and even pronounced in a manageable fashion, such as HEMWat (pronounced "hemwat") and ChMWat (pronounced "kemwat"). Three new solvents join the preceding five in this work: Ac=Acetonitrile, Bu=n-Butanol, and ter=t-Butylmethylether. Typically, solvents are arranged in order of polarity: from least polar to most polar.

Solvent System Family Numbering

An attempt has been made in this work to systematize the solvent system numbering scheme. In this way, solvent systems belonging to different families but bearing the same number share the same ratio of solvents in the order of polarity from least polar to most polar.

All references cited throughout this application, for example patent documents including issued or granted patents or equivalents; patent application publications; and non-patent literature documents or other source material are hereby incorporated by reference in their entireties, as though individually incorporated by reference, to the extent each reference is not inconsistent with the disclosure in this application (for example, a reference that is partially inconsistent is incorporated by reference except for the partially inconsistent portion of the reference).

Every formulation or combination of components described or exemplified herein can be used to practice the invention, unless otherwise stated. Whenever a range is given in the specification, for example a variable range or a concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein may be practiced in the absence of any element or elements, limitation or limitations which is not specifically disclosed herein.

One of ordinary skill in the art will appreciate that materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The Tables

TABLE 1

System numbering and solvent composition of the hexane/ethyl acetate/methanol/water (HEMWat) solvent system family.

| HEMWat System No. | Relative Proportions of Solvents | | | |
|---|---|---|---|---|
| | Hexane | EtOAc | Methanol | Water |
| −8 | 10 | 0 | 10 | 0 |
| −7 | 9 | 1 | 9 | 1 |
| −6 | 8 | 2 | 8 | 2 |
| −5 | 7 | 3 | 7 | 3 |
| −4 | 7 | 3 | 6 | 4 |
| −3 | 6 | 4 | 6 | 4 |
| −2 | 7 | 3 | 5 | 5 |
| −1 | 6 | 4 | 5 | 5 |
| 0 | 5 | 5 | 5 | 5 |
| +1 | 4 | 6 | 5 | 5 |
| +2 | 3 | 7 | 5 | 5 |
| +3 | 4 | 6 | 4 | 6 |
| +4 | 3 | 7 | 4 | 6 |
| +5 | 3 | 7 | 3 | 7 |
| +6 | 2 | 8 | 2 | 8 |
| +7 | 1 | 9 | 1 | 9 |
| +8 | 0 | 10 | 0 | 10 |

TABLE 2

GUESSmix reference standards used herein together with their one-letter abbreviations, molecular formulas, Log Ko/w, and pKa values. Log Ko/w values were obtained from ChemDraw Ultra, with a CS ChemProp Pro add-on. The pKa values were obtained from SPARC calculator v3.1; January 2007 release.

| Letter | Compound | Molecular Formula | Molecular Weight | Log Ko/w | pKa |
|---|---|---|---|---|---|
| r | new coccine red | $C_{20}H_{11}N_2O_{10}S_3Na_3$ | 604.5 | −5.100 | trianion |
| G | chlorogenic acid | $C_{16}H_{18}O_9$ | 354.3 | −1.879 | 3.11 |
| T | L-tryptophan | $C_{11}H_{12}N_2O_2$ | 204.2 | −1.566 | 4.28 |
| H | salicin | $C_{13}H_{18}O_7$ | 286.3 | −1.059 | |
| X | p-arbutin | $C_{12}H_{16}O_7$ | 272.3 | −0.508 | |
| C | caffeine | $C_8H_{10}N_4O_2$ | 194.2 | −0.040 | |
| D | nicotinic acid | $C_6H_5NO_2$ | 123.1 | 0.799 | 4.82 |
| Q | quercetin | $C_{15}H_{10}O_7$ | 302.2 | 0.771 | |

TABLE 2-continued

GUESSmix reference standards used herein together with their one-letter abbreviations, molecular formulas, Log Ko/w, and pKa values. Log Ko/w values were obtained from ChemDraw Ultra, with a CS ChemProp Pro add-on. The pKa values were obtained from SPARC calculator v3.1; January 2007 release.

| Letter | Compound | Molecular Formula | Molecular Weight | Log Ko/w | pKa |
|---|---|---|---|---|---|
| A | aspirin | $C_9H_8O_4$ | 180.2 | 1.023 | 3.38 |
| V | vanillin | $C_8H_8O_3$ | 152.2 | 1.284 | |
| M | coumarin | $C_9H_6O_2$ | 146.2 | 1.412 | |
| F | ferulic acid | $C_{10}H_{10}O_4$ | 194.2 | 1.421 | 4.27 |
| U | umbelliferone | $C_9H_6O_3$ | 162.2 | 1.623 | |
| O | carvone | $C_{10}H_{14}O$ | 150.2 | 2.103 | |
| Z | salicylic acid | $C_7H_6O_3$ | 138.1 | 2.187 | 2.93 |
| N | naringenin | $C_{15}H_{12}O_5$ | 272.3 | 2.445 | |
| E | estradiol | $C_{18}H_{24}O_2$ | 272.4 | 3.225 | |
| R | reserpine | $C_{33}H_{40}N_2O_9$ | 608.7 | 3.264 | |
| I | ionone | $C_{13}H_{20}O$ | 192.3 | 3.770 | |
| Y | cholesterol | $C_{27}H_{46}O$ | 386.7 | 9.520 | |
| b | carotene | $C_{40}H_{56}$ | 536.9 | 15.232 | |

TABLE 3

System numbering and solvent composition of the ethyl acetate/n-butanol/water (EBuWat) solvent system family. Volume ratios represent upper/lower phase.

| EBuWat System No. | Relative Proportions of Solvents | | | Phase Ratio |
|---|---|---|---|---|
| | EtOAc | n-Butanol | Water | |
| −5 | 10 | 0 | 10 | 45/55 |
| −4 | 9 | 1 | 10 | 47/53 |
| −3 | 8 | 2 | 10 | 48/52 |
| −2 | 7 | 3 | 10 | 48/52 |
| −1 | 6 | 4 | 10 | 51/49 |
| 0 | 5 | 5 | 10 | 51/49 |
| +1 | 4 | 6 | 10 | 53/47 |
| +2 | 3 | 7 | 10 | 53/47 |
| +3 | 2 | 8 | 10 | 55/45 |
| +4 | 1 | 9 | 10 | 56/44 |
| +5 | 0 | 10 | 10 | 56/44 |

TABLE 4

System number and solvent composition of the t-butylmethylether/acetonitrile/water (terAcWat) solvent system family. Volume ratios represent upper/lower phase.

| terAcWat System No. | Relative Proportions of Solvents | | | Phase Ratio |
|---|---|---|---|---|
| | MTBE | Acetonitrile | Water | |
| −5 | 10 | 0 | 10 | 45/55 |
| −4 | 9 | 1 | 10 | 43/57 |
| −3 | 8 | 2 | 10 | 41/59 |
| −2 | 7 | 3 | 10 | 38/62 |
| −1 | 6 | 4 | 10 | 36/64 |
| 0 | 5 | 5 | 10 | 34/66 |
| +1 | 4 | 6 | 10 | 33/67 |

TABLE 5

System number and solvent composition of the hexane/t-butylmethylether/acetonitrile/water (HterAcWat) solvent system family. Volume ratios represent upper/lower phase or upper/middle/lower phase.

| HterAcWat System No. | Relative Proportions of Solvents | | | | Phase Ratio |
|---|---|---|---|---|---|
| | Hexane | MTBE | Acetonitrile | Water | |
| −8 | 10 | 0 | 10 | 0 | 40/60 |
| −7 | 9 | 1 | 9 | 1 | 41/59 |
| −6 | 8 | 2 | 8 | 2 | 41/59 |
| −5 | 7 | 3 | 7 | 3 | 43/43/14 |
| −4 | 7 | 3 | 6 | 4 | 45/24/31 |
| −3 | 6 | 4 | 6 | 4 | 44/28/28 |
| −2 | 7 | 3 | 5 | 5 | 47/10/43 |
| −1 | 6 | 4 | 5 | 5 | 46/14/40 |
| 0 | 5 | 5 | 5 | 5 | 51/11/38 |
| +1 | 4 | 6 | 5 | 5 | 63/37 |
| +2 | 3 | 7 | 5 | 5 | 66/34 |
| +3 | 4 | 6 | 4 | 6 | 58/42 |
| +4 | 3 | 7 | 4 | 6 | 59/41 |
| +5 | 3 | 7 | 3 | 7 | 55/45 |
| +6 | 2 | 8 | 2 | 8 | 50/50 |
| +7 | 1 | 9 | 1 | 9 | 49/51 |
| +8 | 0 | 10 | 0 | 10 | 45/55 |

REFERENCES

[1] R. Aman, R. Carle, J. Conrad, U. Beifuss and A. Schieber, J. Chromatogr. A 1074 (2005) 99.
[2] L. Chadwick, R. Fröhlich, S.-N. Chen, J. Bolton, R. van Breemen, C. Overk, J. Burdette, D. Nikolic, H. H. S. Fong, N. Farnsworth and G. F. Pauli, J. Nat. Prod. 67 (2004) 2024.
[3] Q. Du, L. Li and G. Jerz, J. Chromatogr. A 1077 (2005) 98.
[4] Q. W. Du, D.; Ito, Y., J. Liq. Chromatogr. Relat. Technol. 29 (2006) 2587.
[5] X. Han, T. Zhang, Y. Wei, X. Cao and Y. Ito, J. Chromatogr. A 971 (2002) 237.
[6] L. Hua-Bin, K. W. Fan and F. Chen, J. Sep. Sci. 29 (2006) 699.
[7] J. Peng, G. Fan and Y. Wu, J. Chromatogr. A 1091 (2005) 89.
[8] Q. Sun, A. Sun and R. Liu, J. Chromatogr. A 1104 (2006) 69.
[9] Y. Wei, T. Zhang and Y. Ito, J. Chromatogr. A 1033 (2004) 373.
[10] Y. Wei and Y. Ito, J. Chromatogr. A 1115 (2006) 112.
[11] F. Yang, T. Zhang and Y. Ito, J. Chromatogr. A 919 (2001) 443.
[12] P. W. Dalsgaard, J. W. Blunt, M. H. Munro, J. C. Frisvad and C. Christophersen, J. Nat. Prod. 68 (2005) 258.
[13] N. Kohler and P. Winterhalter, J. Chromatogr. A 1072 (2005) 217.
[14] E. Salas, M. Duenas, M. Schwarz, P. Winterhalter, V. Cheynier and H. Fulcrand, J. Agr. Food Chem. 53 (2005) 4536.
[15] Y. Ito, J. Chromatogr. A 1065 (2005) 145.
[16] F. Oka, H. Oka and Y. Ito, J. Chromatogr. 538 (1991) 99.
[17] Y. Gong, J. G. Huang, X. J. Liu and Z. C. Li, J. Liq. Chromatogr. Relat. Technol. 26 (2003) 1509.
[18] A. P. C. Foucault, L., J. Chromatogr. A 808 (1998) 3.
[19] A. Marston and K. Hostettmann, J. Chromatogr. A 1112 (2006) 181.
[20] J. B. Friesen and G. F. Pauli, J. Liq. Chromatogr. Relat. Technol. 28 (2005) 2777.
[21] A. Berthod, M. Hassoun and G. Harris, J. Liq. Chromatogr. Relat. Technol. 28 (2005) 1851.
[22] A. Berthod, J. Chromatogr. A 1126 (2006) 347.

[23] G. F. Pauli and J. B. Friesen, submitted to Anal. Chem. (2006).
[24] A. Berthod, M. J. Ruiz-Angel and S. Carda-Broch, Anal. Chem. 75 (2003) 5886.
[25] A. Berthod, M. Hassoun and M. J. Ruiz-Angel, Anal. Bioanal. Chem. 383 (2005) 327.
[26] W. D. Conway, J. Liq. Chromatogr. Relat. Technol. 24 (2001) 1555.
[27] A. Berthod and B. Billardello, J. Chromatogr. A 902 (2000) 323.
[28] H. T. Lu, Y. Jiang and F. Chen, J. Chromatogr. A 1026 (2004) 185.
[29] J. Y. Peng, G. R. Fan, Z. Y. Hong, Y. F. Chai and Y. T. Wu, J. Chromatogr. A 1074 (2005) 111.
[30] H. B. Li and F. Chen, J. Chromatogr. A 932 (2001) 91.
[31] X. L. Cao, Y. Tian, T. Y. Zhang, X. Li and Y. Ito, J. Chromatogr. A 855 (1999) 709.
[32] X. L. Cao, Y. Tian, T. Y. Zhang, Q. H. Liu, L. J. Jia and Y. Ito, J. Liq. Chromatogr. Relat. Technol. 26 (2003) 1579.
[33] K. Shinomiya, Y. Sasaki, Y. Shibusawa, K. Kishinami, Y. Kabasawa and Y. Ito, J. Liq. Chromatogr. Relat. Technol. 23 (2000) 1575.
[34] K. Shinomiya, Y. Kabasawa and Y. Ito, J. Liq. Chromatogr. Relat. Technol. 24 (2001) 2625.
[35] Q. Z. Du, G. Jerz and P. Winterhalter, J. Chromatogr. A 1045 (2004) 59.
[36] B. K. Gosse, Y. Ito and R. C. Huang, J. Liq. Chromatogr. Relat. Technol. 27 (2004) 1947.
[37] H. Oka, K. I. Harada, M. Suzuki, K. Fujii, M. Iwaya, Y. Ito, T. Goto, H. Matsumoto and Y. Ito, J. Chromatogr. A 989 (2003) 249.
[38] A. Degenhardt, S. Hofmann, H. Knapp and P. Winterhalter, J. Agr. Food Chem. 48 (2000) 5812.
[39] A. Degenhardt, H. Knapp and P. Winterhalter, J. Agr. Food Chem. 48 (2000) 338.
[40] Y. Shibusawa, Y. Yamakawa, R. Noji, A. Yanagida, H. Shindo and Y. Ito, J. Chromatogr. A 1133 (2006) 119.
[41] Y. Shibusawa, A. Yanagida, H. Shindo and Y. Ito, J. Liq. Chromatogr. Relat. Technol. 26 (2003) 1609.
[42] K. Shinomiya and Y. Ito, J. Liq. Chromatogr. Relat. Technol. 29 (2006) 733.

We claim:

1. A method for mapping the polarity range of a solvent system family having two or more biphasic or triphasic solvent systems for use in separation of one or more chemical components of a mixture by counter-current chromatography which comprises the steps of:
   (a) providing a reference mixture of reference natural products wherein the reference mixture comprises at least three structurally distinct chemical species of different polarity and different molecular mass wherein the mixture comprises at least one hydrophilic component and at least one lipophilic component;
   (b) selecting a plurality of biphasic or triphasic solvent systems of the solvent system family wherein the plurality of biphasic of triphasic solvent systems spans the range of relative proportions of the solvent components of the solvent system family; and
   (c) determining the distribution constant ($K_D$) for each reference natural product in each selected biphasic or triphasic solvent system of the solvent system family, thereby mapping the polarity range of the solvent system family.

2. The method of claim 1 wherein the solvent systems of the solvent family are biphasic solvent systems.

3. The method claim 1 wherein the reference mixture comprises three or more reference components selected from the group consisting of new coccine red, carotene, cholesterol, ionone, reserpine, estradiol, naringenin, salicylic acid, carvone, umbelliferone, ferulic acid, coumarin, vanillin, aspirin, quercetin, nicotinic acid, caffeine, p-arbutin, salicin, L-tryptophan, and chlorogenic acid.

4. The method of claim 1 wherein the reference mixture comprises new coccine red, carotene, cholesterol, ionone, reserpine, estradiol, naringenin, salicylic acid, carvone, umbelliferone, ferulic acid, coumarin, vanillin, aspirin, quercetin, nicotinic acid, caffeine, p-arbutin, salicin, L-tryptophan, and chlorogenic acid.

5. The method of claim 1 wherein the reference mixture comprises carotene, carvone, estradiol, salicyclic acid, naringenin, coumarin, umbelliferone, quercitin, ferulic acid, vanillin, caffeine and new coccine red.

6. A method for selecting one or more biphasic or triphasic solvent systems of one or more solvent families for use in counter-current chromatography for the separation of two or more chemical components of a target mixture which comprises the steps of:
   (a) mapping the polarity range of the one or more biphasic or triphasic solvent systems of the one or more solvent system families employing a reference mixture of reference natural products by the method of claim 1 and thereby determining which reference components of the reference mixture have $K_D$ in the one or more mapped solvent systems ranging from 0.25 to 16;
   (b) determining the $K_D$s of the two or more of the chemical components of the target mixture relative to at least one of the components of the reference mixture that have $K_D$ ranging from 0.25 to 16 in the one or more mapped solvent systems by liquid chromatograph, thin layer chromatography or gas chromatography;
   (c) determining which of the reference components that have $K_D$ in the one or more mapped solvent systems ranging from 0.25 to 16 match the relative $K_D$s of the two or more components of the target mixture; and
   (d) selecting the one or more solvent systems for use in separation of the two or more components of the target system in which there is a relative $K_D$ match between the two or more components of the target mixture and the one or more reference components.

7. The method of claim 6 wherein the target mixture comprises more than two chemical components.

8. The method of claim 6 wherein determination of relative polarities, relative $K_D$s or both are determined by determining relative Rf values employing thin layer chromatography.

9. The method of claim 8 wherein a match of relative Rf values is defined by relative Rf values between 3 and 0.33.

10. The method of claim 8 wherein a match of relative Rf values is defined by relative Rf values between 2 and 0.5.

11. The method of claim 8 wherein a match of relative Rf values is defined by relative Rf values between 1.25 and 0.75.

12. The method of claim 6 wherein the reference components used for the determination of relative polarities or relative $K_D$s are those having the highest and lowest $K_D$s within the range of $K_D$s from 0.25 to 16 in a given biphasic or triphasic solvent system.

13. The method of claim 6 wherein one or more biphasic or triphasic solvent systems are selected for separation of more than two components of the target mixture.

14. The method of claim 6 wherein the reference components are selected from the group consisting of new coccine red, carotene, cholesterol, ionone, reserpine, estradiol, naringenin, salicylic acid, carvone, umbelliferone, ferulic acid, coumarin, vanillin, aspirin, quercetin, nicotinic acid, caffeine, p-arbutin, salicin, L-tryptophan, and chlorogenic acid.

15. The method of claim 6 wherein the solvent system is a biphasic or triphasic solvent system of a solvent system family selected from the group consisting of HEMWat, EBuWat, terAcWat, and HterAcWat.

16. A method for carrying out a counter-current chromatography separation of two or more chemical components of a target mixture which comprises the steps of selecting one or more biphasic or triphasic solvent systems of one or more solvent families by the method of claim 6 and carrying out the separation employing the selected one or more biphasic or triphasic solvent systems.

17. The method of claim 16 wherein the target mixture is a mixture of natural products.

18. The method of claim 6 wherein the solvent systems of the solvent family are biphasic.

* * * * *